United States Patent
Nadig et al.

(10) Patent No.: US 10,647,491 B2
(45) Date of Patent: *May 12, 2020

(54) FOLDABLE SLEEVE FOR SURGICAL INSTRUMENT

(71) Applicant: Covidien LP, Mansfield, MA (US)

(72) Inventors: Divya Vijaya Vittala Nadig, Hamden, CT (US); Dharani Gandhi, Tamil Nadu (IN)

(73) Assignee: Covidien LP, Mansfield, MA (US)

( * ) Notice: Subject to any disclaimer, the term of this patent is extended or adjusted under 35 U.S.C. 154(b) by 143 days.

This patent is subject to a terminal disclaimer.

(21) Appl. No.: 15/689,226

(22) Filed: Aug. 29, 2017

(65) Prior Publication Data

US 2017/0355505 A1    Dec. 14, 2017

Related U.S. Application Data

(63) Continuation of application No. 14/730,504, filed on Jun. 4, 2015, now Pat. No. 9,776,783.

(51) Int. Cl.
*A61B 50/30* (2016.01)
*A61B 50/20* (2016.01)
*B65D 77/04* (2006.01)

(52) U.S. Cl.
CPC .............. *B65D 77/04* (2013.01); *A61B 50/30* (2016.02); *A61B 50/20* (2016.02); *A61B 2050/314* (2016.02)

(58) Field of Classification Search
CPC .............. A61B 2050/314; A61B 50/20; B65D 73/0021; B65D 77/04

USPC ........ 206/363–364, 438, 464, 476–477, 482, 206/485, 571, 495

See application file for complete search history.

(56) References Cited

U.S. PATENT DOCUMENTS

| | | |
|---|---|---|
| 3,951,333 A | 4/1976 | Forbes, Jr. et al. |
| 4,023,678 A | 5/1977 | Fiedler |
| 4,111,302 A | 9/1978 | Roth |
| 4,121,711 A | 10/1978 | Bolanowski |
| 4,332,322 A | 6/1982 | Jaeschke et al. |
| 4,483,437 A | 11/1984 | Cerwin et al. |
| 4,884,681 A | 12/1989 | Roshdy et al. |
| 5,024,322 A | 6/1991 | Holzwarth |
| 5,121,836 A * | 6/1992 | Brown ............. A61B 17/06138 206/438 |
| 5,127,518 A | 7/1992 | Holzwarth et al. |
| 5,199,561 A | 4/1993 | Roshdy et al. |
| 5,220,769 A | 6/1993 | Brown et al. |

(Continued)

FOREIGN PATENT DOCUMENTS

EP    0664991 A2    8/1995

OTHER PUBLICATIONS

European Search Report EP16172833 dated Aug. 8, 2016.

*Primary Examiner* — Steven A. Reynolds

(57) ABSTRACT

A foldable sleeve for retaining a surgical instrument is presented. The foldable sleeve includes a first panel having a first set of lock tabs, a second panel hingedly connected to the first panel, the second panel having a first pair of openings and a second pair of openings, and a third panel hingedly connected to the second panel, the third panel having a second set of lock tabs. The first panel and the third panel are each selectively movable over a portion of the second panel to retain the surgical instrument within the foldable sleeve.

5 Claims, 10 Drawing Sheets

(56) References Cited

U.S. PATENT DOCUMENTS

| | | | |
|---|---|---|---|
| 5,226,535 | A | 7/1993 | Rosdhy et al. |
| 5,249,672 | A | 10/1993 | Brown et al. |
| 5,358,624 | A | 10/1994 | Roshdy et al. |
| 5,375,717 | A | 12/1994 | Roshdy |
| 5,392,909 | A | 2/1995 | Hackett |
| 5,425,445 | A | 6/1995 | Brown et al. |
| 5,447,230 | A | 9/1995 | Gerondale |
| 5,487,469 | A | 1/1996 | Roshdy et al. |
| 5,501,341 | A | 3/1996 | Van Es |
| 5,529,175 | A * | 6/1996 | Brunken .......... A61B 17/06138 206/63.3 |
| 5,542,539 | A | 8/1996 | Early |
| 5,566,821 | A | 10/1996 | Brown et al. |
| 5,655,657 | A | 8/1997 | Roshdy |
| 5,699,909 | A | 12/1997 | Foster |
| 5,746,311 | A * | 5/1998 | Brown ............. A61B 17/06138 206/388 |
| 5,788,063 | A | 8/1998 | Van Ness |
| 5,833,055 | A | 11/1998 | Cerwin et al. |
| 5,896,982 | A * | 4/1999 | Surcin .............. A61B 17/06138 206/63.3 |
| 5,941,384 | A | 8/1999 | Schonhardt et al. |
| 5,947,284 | A | 9/1999 | Foster |
| 5,954,202 | A | 9/1999 | Mellon |
| 5,957,289 | A | 9/1999 | Negelen |
| 6,045,035 | A * | 4/2000 | Murakami ............. B65D 27/22 206/388 |
| 6,719,128 | B2 | 4/2004 | Alpern et al. |
| 6,814,236 | B2 | 11/2004 | Roshdy |
| 7,549,270 | B2 | 6/2009 | Rowe et al. |
| 7,600,634 | B2 | 10/2009 | Malinowski et al. |
| 8,128,859 | B2 | 3/2012 | Dey et al. |
| 8,136,656 | B2 | 3/2012 | Kennedy et al. |
| 8,226,669 | B2 | 7/2012 | Detruit et al. |
| 8,413,810 | B2 | 4/2013 | Merboth et al. |
| 2005/0211595 | A1 | 9/2005 | Hull |
| 2007/0209957 | A1 | 9/2007 | Glenn et al. |
| 2012/0061262 | A1 * | 3/2012 | Merboth ................ A61B 50/30 206/204 |
| 2014/0174973 | A1 | 6/2014 | Bailey |
| 2014/0353198 | A1 | 12/2014 | Bradfield |

\* cited by examiner

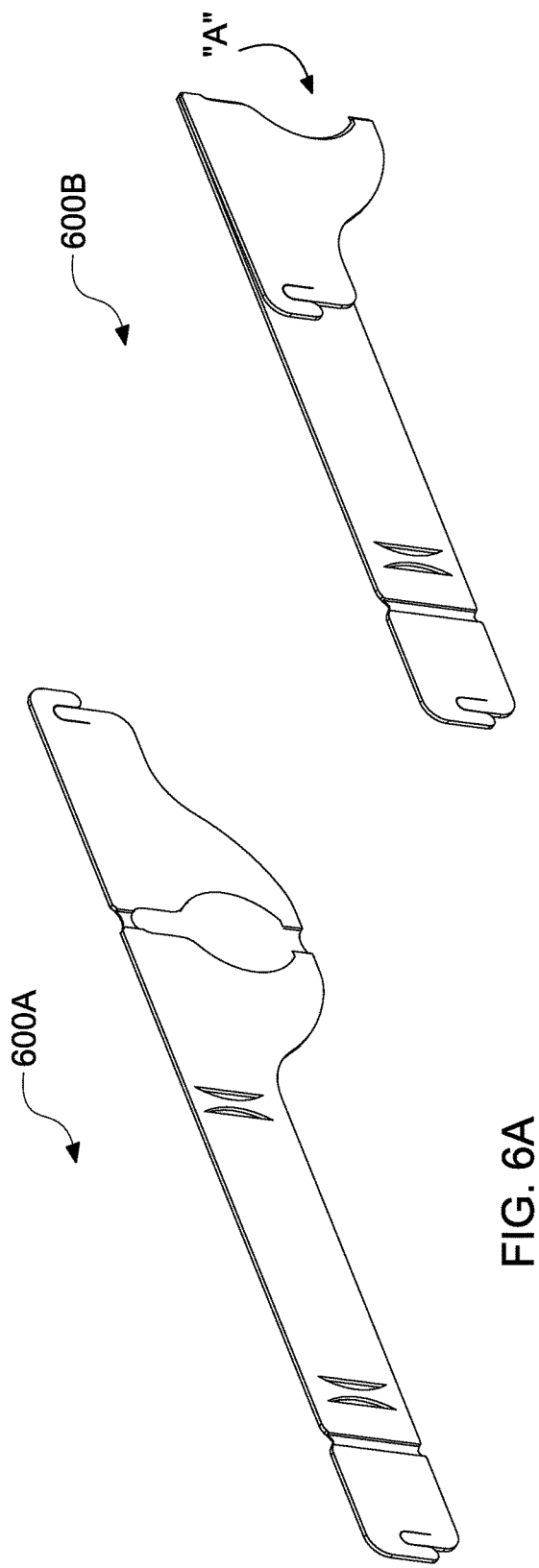
FIG. 6A
FIG. 6B
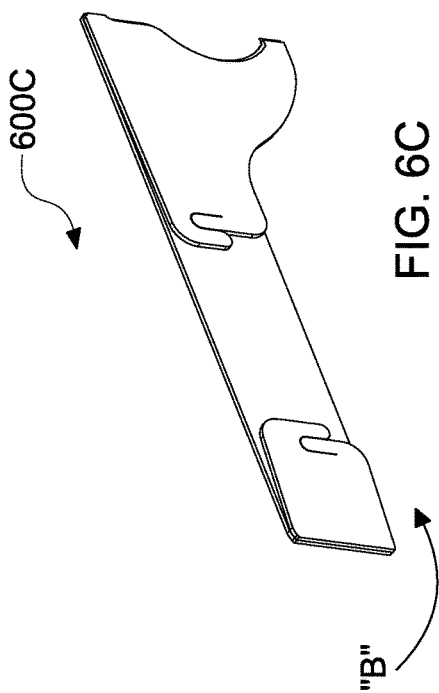
FIG. 6C

FOLDABLE SLEEVE FOR SURGICAL INSTRUMENT

CROSS-REFERENCE TO RELATED APPLICATIONS

This application is a continuation of U.S. patent application Ser. No. 14/730,504 filed Jun. 4, 2015, and the disclosure of the above-identified application is hereby incorporated by reference in its entirety.

TECHNICAL FIELD

The present disclosure relates to packaging products for surgical instruments. More particularly, the present disclosure relates to a foldable sleeve for a surgical instrument.

BACKGROUND OF RELATED ART

Wrap-around storage containers are well-known. When fabricating a storage container from a paperboard blank, opposite sides of the blank are attached to each other by glue or by mechanical locks to form the bottom panel of the storage container. In the case of a wrap-around storage container, flaps located on the sides of the blank typically are overlapped and engaged with one another by mechanical locks formed in the flaps to form the bottom panel of the storage container. Since the bottom panel must maintain its integrity throughout the use of the storage container, it is essential that the locking system be capable of supporting the weight of the packaged articles, and remain engaged during shipping and handling of the constructed storage container.

Surgical instruments have been known to be packaged in a similar configuration called a "blister." Blister packages, which are also called "blister packs," are known in a wide variety of embodiments. In the previously known blister packages, a product which is also intended as an insert or accessory part is usually packaged visibly. To this end, the previously known blister packages have a plastic film molded part which is manufactured from transparent plastic film and supports the product to be packaged in a molded cavity which is made in the plastic film. Blister packages of this type allow the customer or purchaser to see the packaged article. The product is presented in front of a cardboard wall and is fixed with the plastic film molded part.

However, it is often considered to be disadvantageous that the blister packaging becomes unusable after being opened for the first time and must be disposed of as packaging waste. Additionally, it is disadvantageous that the blister packaging does not allow a user to handle the item when it is packaged therein. Thus, it would be advantageous to provide a reconfigured packaging product that allows a user to access or manipulate an item enclosed therein.

SUMMARY

The present disclosure relates to a foldable sleeve for retaining a surgical instrument. The foldable sleeve includes a first panel having a first set of lock tabs, a second panel hingedly connected to the first panel, the second panel having a first pair of openings and a second pair of openings, and a third panel hingedly connected to the second panel, the third panel having a second set of lock tabs. The first panel and the third panel are each selectively movable over a portion of the second panel to retain the surgical instrument within the foldable sleeve.

In disclosed embodiments, the second panel may be hingedly connected to the first panel via a first folding portion and the third panel may be hingedly connected to the second panel via a second folding portion.

In disclosed embodiments, the first and second folding portions may each include a plurality of creases.

In disclosed embodiments, the second folding portion may extend continuously along a junction between the third panel and the second panel.

In disclosed embodiments, the first folding portion may be separated into two sections by a first aperture. The first aperture may be formed at a junction between the first panel and the second panel.

In disclosed embodiments, the first aperture has a first end having a first size and a second end having a second size, the second size being greater than the first size.

In disclosed embodiments, the first pair of openings and the second pair of openings retain a shaft portion of the surgical instrument.

In disclosed embodiments, the first set of lock tabs may lock against a first section of a shaft of the surgical instrument and the second set of lock tabs may lock against a second section of the shaft of the surgical instrument to retain the surgical instrument within the foldable sleeve.

In disclosed embodiments, the first panel has a first size, the second panel has a second size, and the third panel has a third size, the first, second, and third sizes being different from each other.

In disclosed embodiments, the foldable sleeve includes a top end, a bottom end, and two side ends, the top end being substantially linear and the bottom end having at least two inclined sections.

In disclosed embodiments, the foldable sleeve may retain a single article therein.

The present disclosure relates to a foldable sleeve for retaining a surgical instrument. The foldable sleeve includes a first panel, a second panel, and a third panel arranged in a series configuration, such that the second panel is hingedly connected to the first panel and the third panel is hingedly connected to the second panel. The first panel folds over a first section of the second panel and the third panel folds over a second section of the second panel to retain the surgical instrument.

The present disclosure further relates to a foldable sleeve for retaining a surgical instrument. The foldable sleeve includes a plurality of panels arranged in a series configuration, the plurality of panels hingedly connected to each other, and at least one of the plurality of panels includes a set of locking tabs. The surgical instrument is configured to be removed from the foldable sleeve without unlocking the set of locking tabs.

The present disclosure further relates to a sleeve for retaining a surgical instrument. The sleeve includes a first panel, a second panel, and a third panel arranged in a series configuration, and hingedly connected to each other, a set of locking tabs disposed on at least one of the first, second, and third panels, and an opening defined on at least one of the panels, the opening configured to expose at least a portion of the surgical instrument. The surgical instrument is configured to be removed from the opening of the sleeve without unlocking the set of locking tabs and without transitioning the sleeve to an unfolded configuration.

The present disclosure further relates to a method of securing a surgical instrument within a foldable sleeve. The method includes the steps of hingedly connecting a second panel to a first panel and a third panel, incorporating a first set of openings and a second set of openings on the second panel, folding the first panel having a first set of lock tabs onto a portion of the second panel, and folding the third panel having a second set of lock tabs onto a portion of the second panel.

The present disclosure further relates to a method of securing a surgical instrument within a foldable sleeve. The method includes the steps of providing a first panel having a first set of lock tabs, providing a second panel hingedly connected to the first panel, the second panel having a first pair of openings and a second pair of openings, and providing a third panel hingedly connected to the second panel, the third panel having a second set of lock tabs. The method further includes the step of selectively moving the first and third panels over a portion of the second panel to retain the surgical instrument within the foldable sleeve.

A kit is also provided in accordance with the present disclosure. The kit includes a package containing at least one surgical instrument and at least one foldable sleeve configured to retain the at least one surgical instrument. The at least one surgical instrument is one of a grasper, cutter, scissor, clip applier, stapler, dissector, retractor, access device, clamping device, vessel expanding device, biopsy device, drug/gene therapy delivery device, energy delivery device, and a drill. The package may also include instructions for use.

DESCRIPTION OF THE DRAWINGS

The above and other aspects, features, and advantages of the present disclosure will become more apparent in light of the following detailed description when taken in conjunction with the accompanying drawings in which:

FIGS. 6A-6C illustrate how the foldable sleeve is transitioned from the unfolded configuration to the folded configuration, in accordance with the embodiments of the present disclosure.

DETAILED DESCRIPTION

Figure 1:
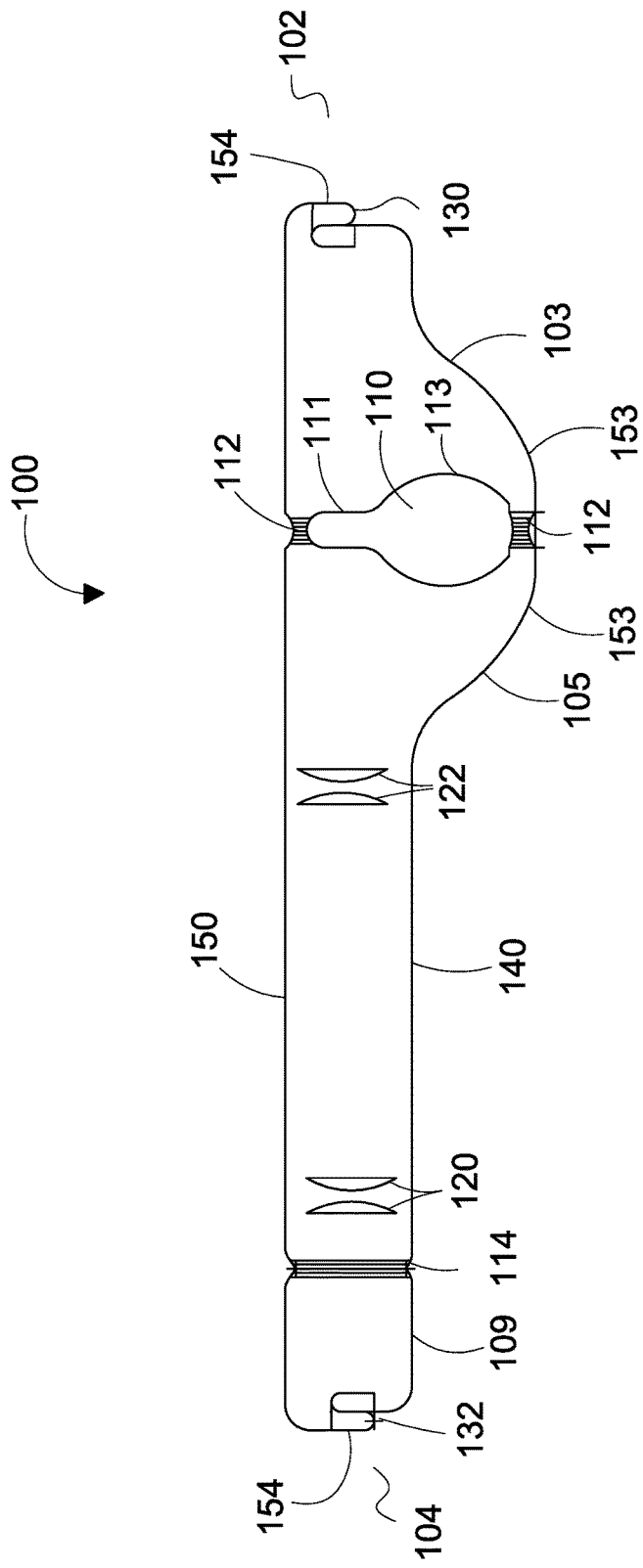
FIG. 1 illustrates a foldable sleeve in an unfolded configuration, in accordance with the embodiments of the present disclosure.

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

Reference will now be made in detail to embodiments of the present disclosure. While certain exemplary embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

FIG. 1 illustrates a foldable sleeve 100 in an unfolded configuration, in accordance with the embodiments of the present disclosure.

The foldable sleeve 100 includes a first panel 103, a second panel 105, and a third panel 109. The foldable sleeve 100 has a proximal end 102 and a distal end 104. The foldable sleeve 100 has a top end 150, a bottom end 140, and side ends 154. The top end 150 is substantially linear, whereas the bottom end 140 has at least two inclined portions 153. The foldable sleeve 100 is configured to retain a single article or item therein. Preferably, the article or item is a surgical instrument 200, as described below with reference to FIG. 2. The foldable sleeve 100 is shown in a first configuration or an unfolded configuration. The foldable sleeve 100 may be, for example, a paperboard sleeve. Of course, one skilled in the art may contemplate other materials for forming or manufacturing the foldable sleeve 100, such as from cardboard and plastics.

The first panel 103 includes a first set of lock tabs 130. The first panel 103 is hingedly connected to the second panel 105 by a first folding portion 112. Additionally, the first panel 103 is separated from the second panel 105 by an aperture 110. The aperture 110 includes a first end 111 and a second end 113. The first end 111 has a first size, whereas the second end 113 has a second size. The second size is greater than the first size. Further, the first folding portion 112 includes two sections that are separated by the aperture 110. The two sections are located on opposed ends of the aperture 110. The first folding section 112 has a plurality of creases. The first panel 103 has a substantially irregular shape.

The second panel 105 includes a first pair of openings 120 and a second pair of openings 122. The first and second pair of openings 120, 122 are configured to receive a shaft portion of a surgical instrument 200 therethrough (see FIG. 2). The second panel 105 is hingedly connected to the third panel 109 by a second folding portion 114. The second folding portion 114 extends continuously along a junction between the second panel 105 and the third panel 109. The first panel 103 has a first size, whereas the second panel 105 has a second size. The second size is greater than the first size. In fact, the second panel 105 defines an elongated portion for accommodating a shaft of a surgical instrument 200 (see FIG. 2). The second folding section 114 has a plurality of creases.

The third panel 109 includes a second set of lock tabs 132. The third panel 109 is hingedly connected to the second panel 105 by the second folding portion 114. The third panel 109 has a third size, the third size being different than the first and second sizes of the first and second panels 103, 105, respectively. The third panel 109 has a substantially rectangular shape. The first panel 103, the second panel 105, and the third panel 109 are arranged in a series configuration.

Figure 2:
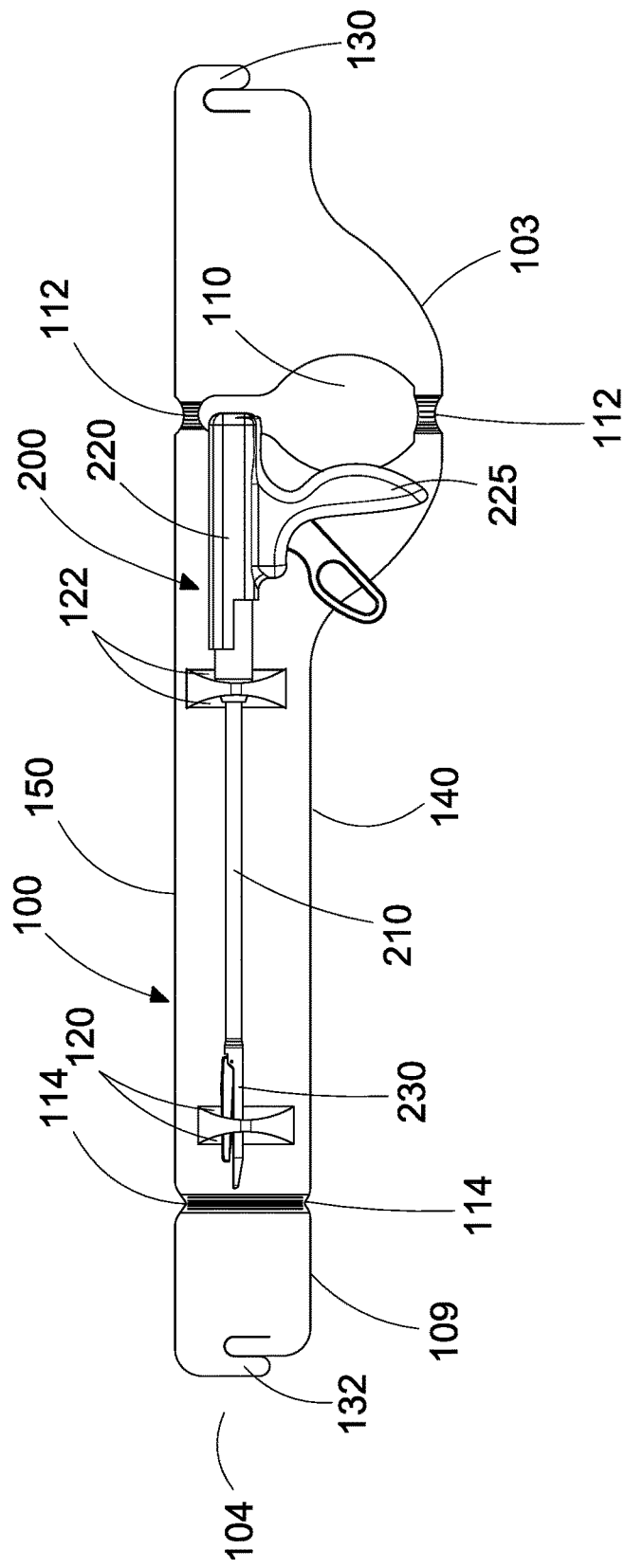
FIG. 2 illustrates a surgical instrument placed onto the foldable sleeve of FIG. 1, in accordance with the embodiments of the present disclosure.

FIG. 2 illustrates a surgical instrument 200 placed onto the foldable sleeve 100 of FIG. 1, in accordance with the embodiments of the present disclosure.

The surgical instrument 200 includes a shaft or shaft portion 210. A proximal end of the shaft portion 210 is attached to a body portion 220 having a handle portion 225. The distal end of the shaft portion 210 is attached to an end effector 230. The end effector 230 may include, for example, a pair of jaws. In FIG. 2, the surgical instrument 200 is placed or positioned on the foldable sleeve 100 such that the shaft portion 210 is placed over or on top of the elongated portion of the second panel 105 of the foldable sleeve 100. The end effector 230 is placed over or on top of the distal end of the second panel 105. The body portion 220 and the handle portion 225 are placed over or on top of the proximal end of the second panel 105. The shaft portion 210 is inserted through openings 120, 122 to help hold the surgical instrument 200 to the foldable sleeve 100. In an alternative embodiment, the first pair of openings 120 may be defined on the third panel 109 and the second pair of openings 122 may be defined on the first panel 103 to retain the shaft portion 210 of the surgical instrument 200. One skilled in the art may provide openings for retaining the shaft portion 210 of the surgical instrument 200 on any portion of the foldable sleeve 100. For example, openings may be provided on all three panels, 103, 105, and 109. Further, the first and second set of locking tabs 130, 132 may be disposed on any portion of the first, second, and third panels 103, 105, and 109. One skilled in the art may contemplate a number of different positional configurations for first and second locking tabs 130, 132.

Figure 3A:
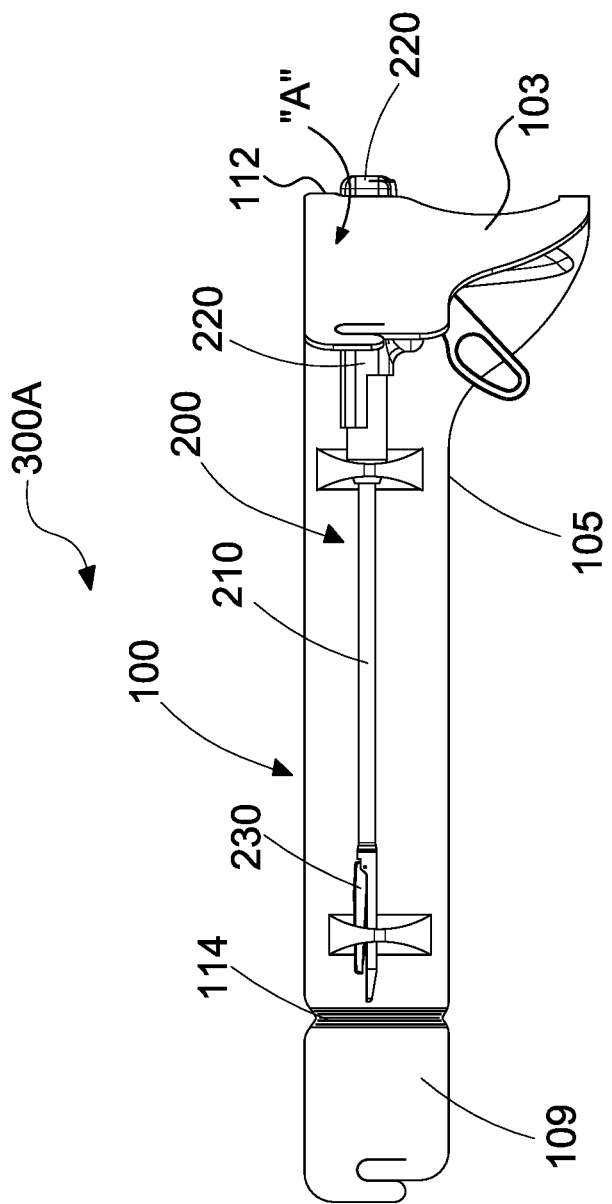
FIG. 3A illustrates one panel of the foldable sleeve partially folded onto a portion of the surgical instrument, in accordance with the embodiments of the present disclosure.
Figure 3B:
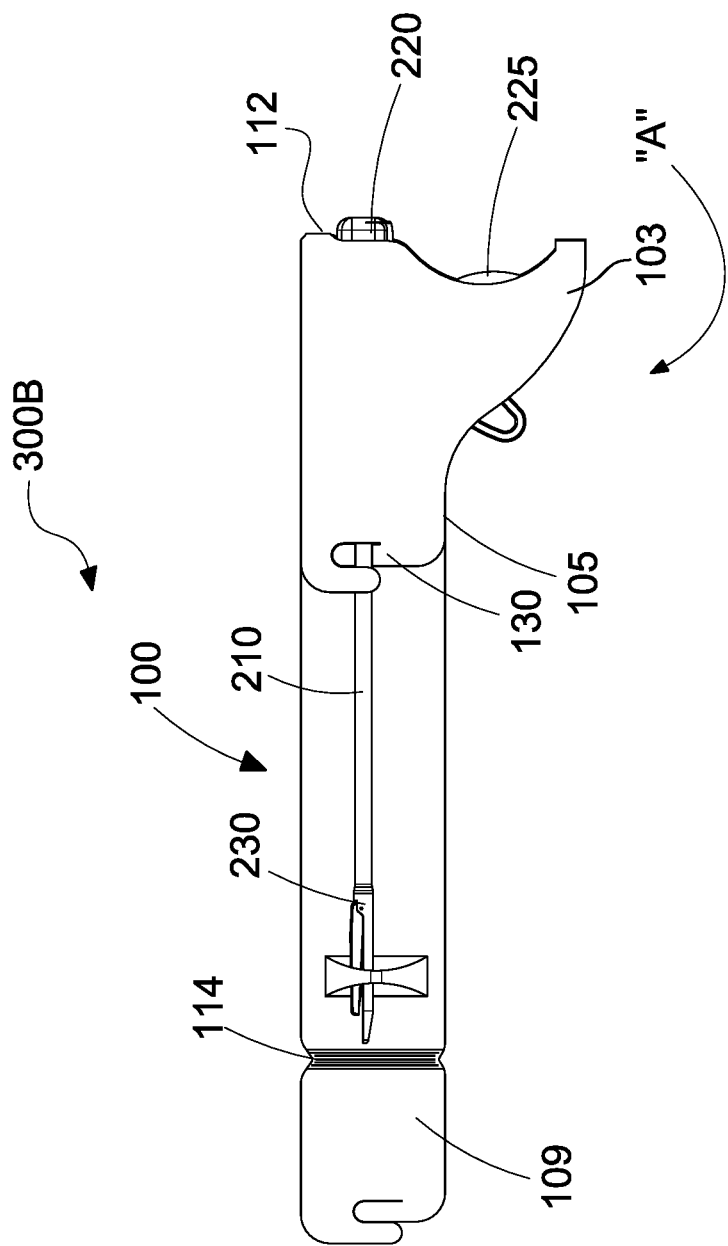
FIG. 3B illustrates the panel of FIG. 3A completely folded over the portion of the surgical instrument, in accordance with the embodiments of the present disclosure.

FIG. 3A illustrates a first configuration 300A where one panel 103 of the foldable sleeve 100 is partially folded onto a portion of the surgical instrument 200, in accordance with the embodiments of the present disclosure and FIG. 3B illustrates a second configuration 300B where the panel 103 of FIG. 3A is completely folded over the portion of the surgical instrument 200, in accordance with the embodiments of the present disclosure.

In operation, once the surgical instrument 200 is placed over or on top of the foldable 100, a user may fold the first panel 103 onto a portion of the second panel 105. The fold occurs at the first folding portion 112 which includes a plurality of creases. The fold allows for the creation of a space at the right side of the foldable sleeve 100 such that the handle portion 225 of the surgical instrument is partially visible. The fold occurs in the direction "A." The first set of lock tabs 130 locks against a first section of the shaft portion 210 of the surgical instrument 200. The shaft portion 210 is secured in place by the first set of lock tabs 130.

Figure 4A:
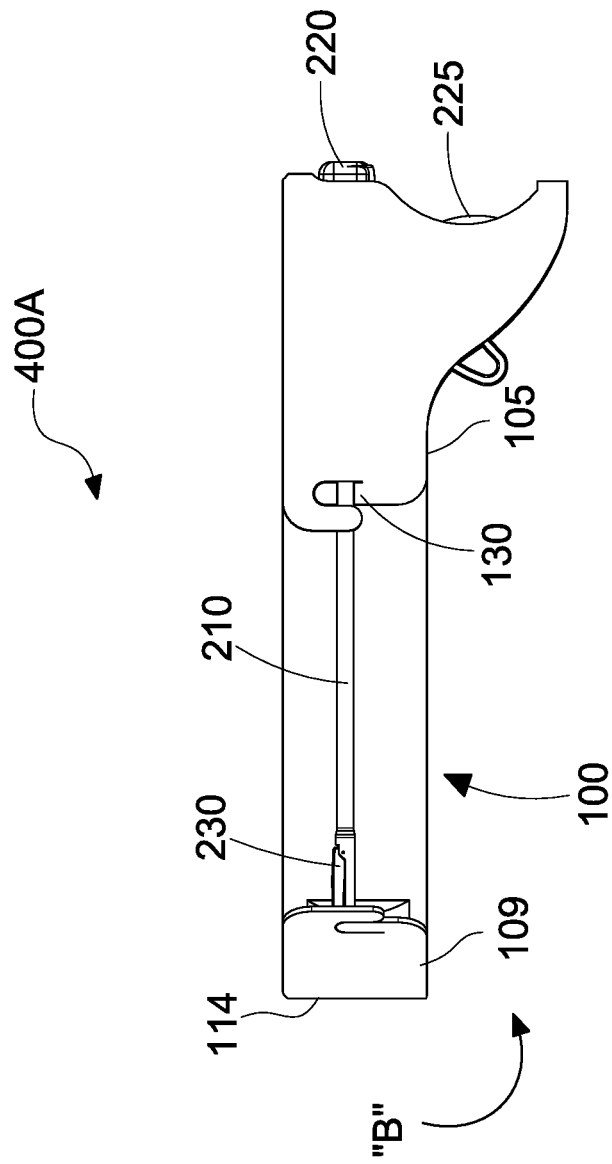
FIG. 4A illustrates another panel of the foldable sleeve partially folded onto another portion of the surgical instrument, in accordance with the embodiments of the present disclosure.
Figure 4B:
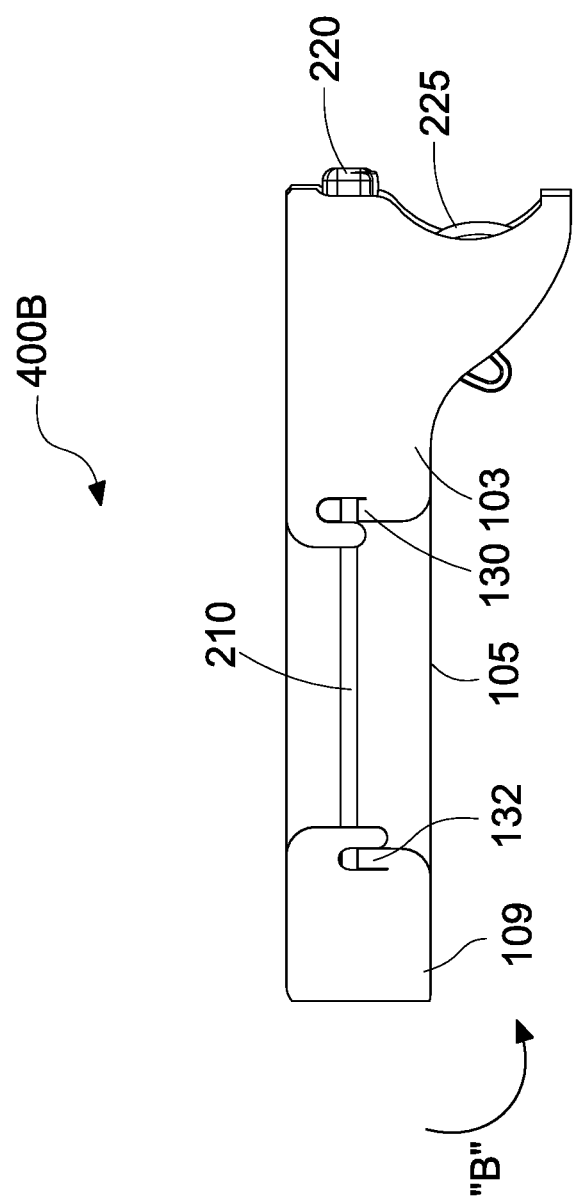
FIG. 4B illustrates the panel of FIG. 4A completely folded over the other portion of the surgical instrument, in accordance with the embodiments of the present disclosure.

FIG. 4A illustrates a first configuration 400A of the other panel 109 of the foldable sleeve 100 partially folded onto another portion of the surgical instrument 200, in accordance with the embodiments of the present disclosure and FIG. 4B illustrates a second configuration 400B of the panel 109 of FIG. 4A completely folded over the other portion of the surgical instrument 200, in accordance with the embodiments of the present disclosure.

In operation, once the surgical instrument 200 is placed over or on top of the foldable sleeve 100, a user may fold the third panel 109 onto a portion of the second panel 105. The fold occurs at the second folding portion 114 which includes a plurality of creases. The fold does not allow for the creation of a space (as was the occurrence with the fold at first folding section 112) at the left side of the foldable sleeve 100. The fold occurs in the direction "B." The second set of lock tabs 132 locks against a second section of the shaft portion 210 of the surgical instrument 200. Thus, in FIGS. 3A and 3B, the first set of lock tabs 130 locks against a first section of the shaft portion 210 of the surgical instrument 200 and in FIGS. 4A and 4B, the second set of lock tabs 132 locks against a second section of the shaft portion 210 of the surgical instrument 200 to retain the surgical instrument 200 within the foldable sleeve 100. This is referred to as the second configuration or the folded configuration. The locking tabs 130, 132 inhibit movement away from the sleeve 100, but allow sliding movement along the long axis of the sleeve 100.

Once the first panel 103 and the third panel 109 are folded over at least a portion of the second panel 105, the surgical instrument 200 is encased or enveloped or held within the foldable sleeve 100 in a folded configuration. However, a portion of the handle portion 225 is visible and accessible to a user (see FIGS. 5A-5C). A section of the shaft portion 210 of the surgical instrument 200 is also visible in the folded configuration. Additionally, in the folded configuration, a window 410 is visible for displaying the product name and any other relevant information.

Each foldable sleeve 100 includes a single surgical instrument 200 therein. Each foldable sleeve 100 is packaged within a foil pouch (not shown). Each foil pouch containing a foldable sleeve 100 is packaged with a box. The box may contain one or more foil pouches. In use, the box is shipped to, for example, a hospital where the box is opened to remove the foil pouches to be stored. When a surgical procedure is performed, the OR is prepared by providing the surgeons with one or more surgical instruments 200 each retained with a foldable sleeve 100 packaged within a foil pouch. The surgeon or nurse or other medical personnel opens the foil pouch to expose the sleeve 100 retaining the surgical instrument 200. The sleeve 100 protects the surgical instrument 200 until the time of use. Once the surgeon desires to access the surgical instrument 200, the surgical instrument 200 may be removed from the sleeve 100 as described below with reference to FIGS. 5A-5C.

Figure 5A:
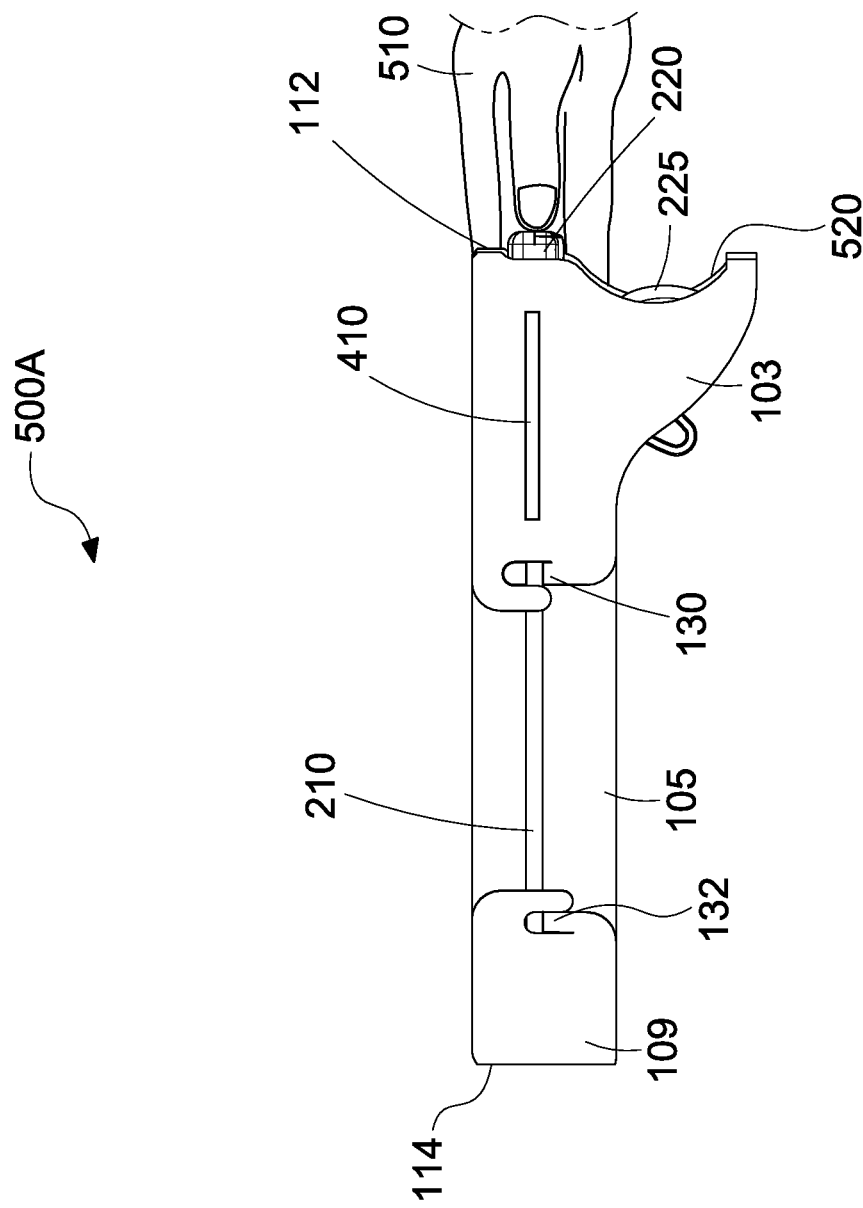
FIG. 5A illustrates a user holding the handle portion of the surgical instrument when the foldable sleeve is in the folded configuration, in accordance with the embodiments of the present disclosure.
Figure 5B:
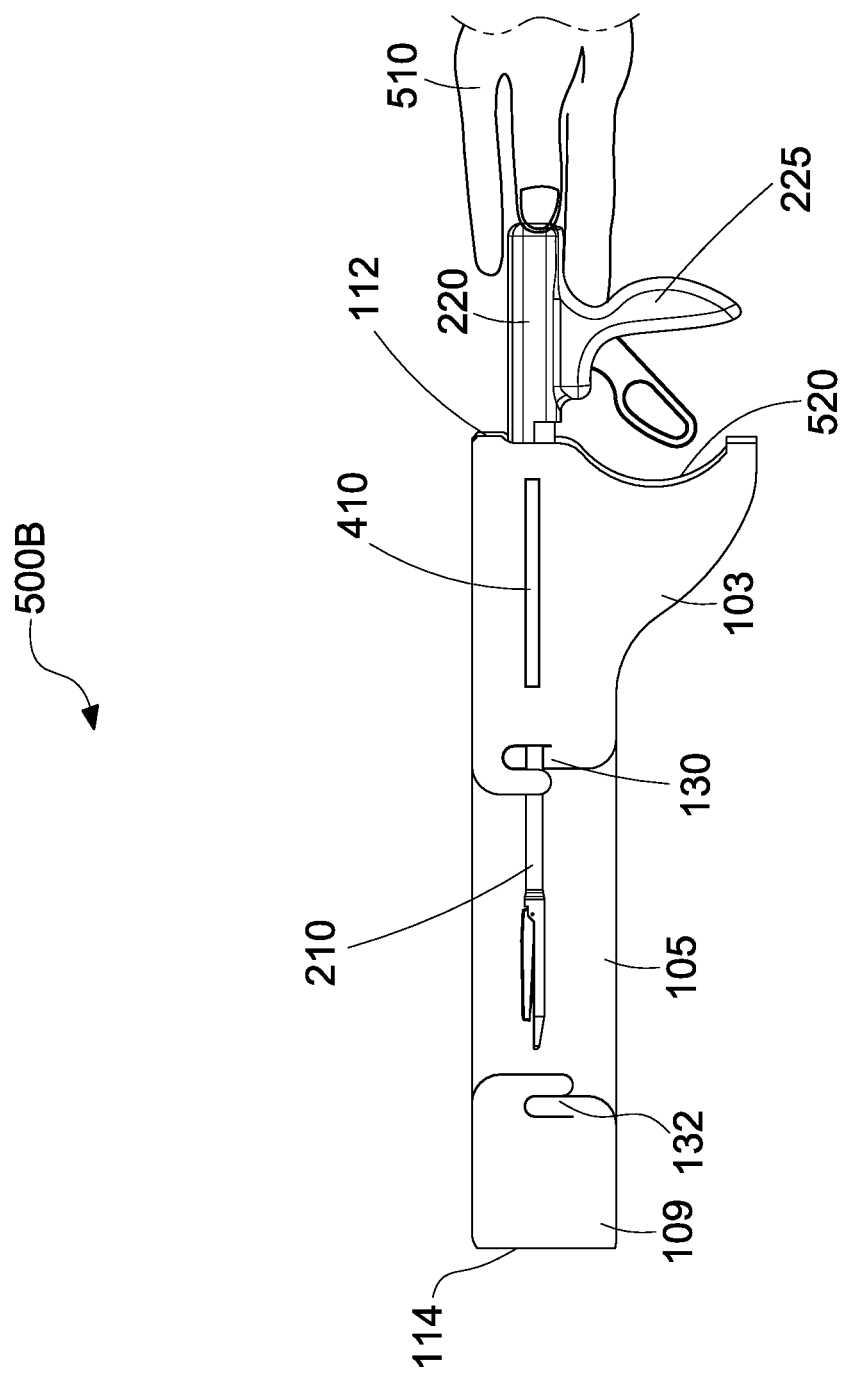
FIG. 5B illustrates a user pulling on the handle portion of the surgical instrument when the foldable sleeve is in the folded configuration, and partially removing the surgical instrument, in accordance with the embodiments of the present disclosure.

FIG. 5A illustrates a first configuration 500A, where a user's hand 510 holds the body portion 220 of the surgical instrument 200 when the foldable sleeve 100 is in the folded configuration, in accordance with the embodiments of the present disclosure and FIG. 5B illustrates a second configuration 500B where the user's hand 510 pulls on the body portion 220 of the surgical instrument 200 when the foldable sleeve 100 is in the folded configuration, and the hand 510 partially removing the surgical instrument 200 from the foldable sleeve 100, in accordance with the embodiments of the present disclosure.

The user's hand 510 may access either the body portion 220 or the handle portion 225 and pull or remove the surgical instrument 200 from the opening 520 of the foldable sleeve 100 without having to undo or unwrap the foldable sleeve 100 and without having to unlock the sets of tabs 130, 132. Therefore, the user may simply slide the surgical instrument 200 out of the opening 520 of the foldable sleeve 100 without disturbing the folded configuration of the foldable sleeve 100. This allows the surgical instrument 200 to be properly protected in a sterile environment and simultaneously allows for easy accessibility of the surgical instrument 200.

Figure 5C:
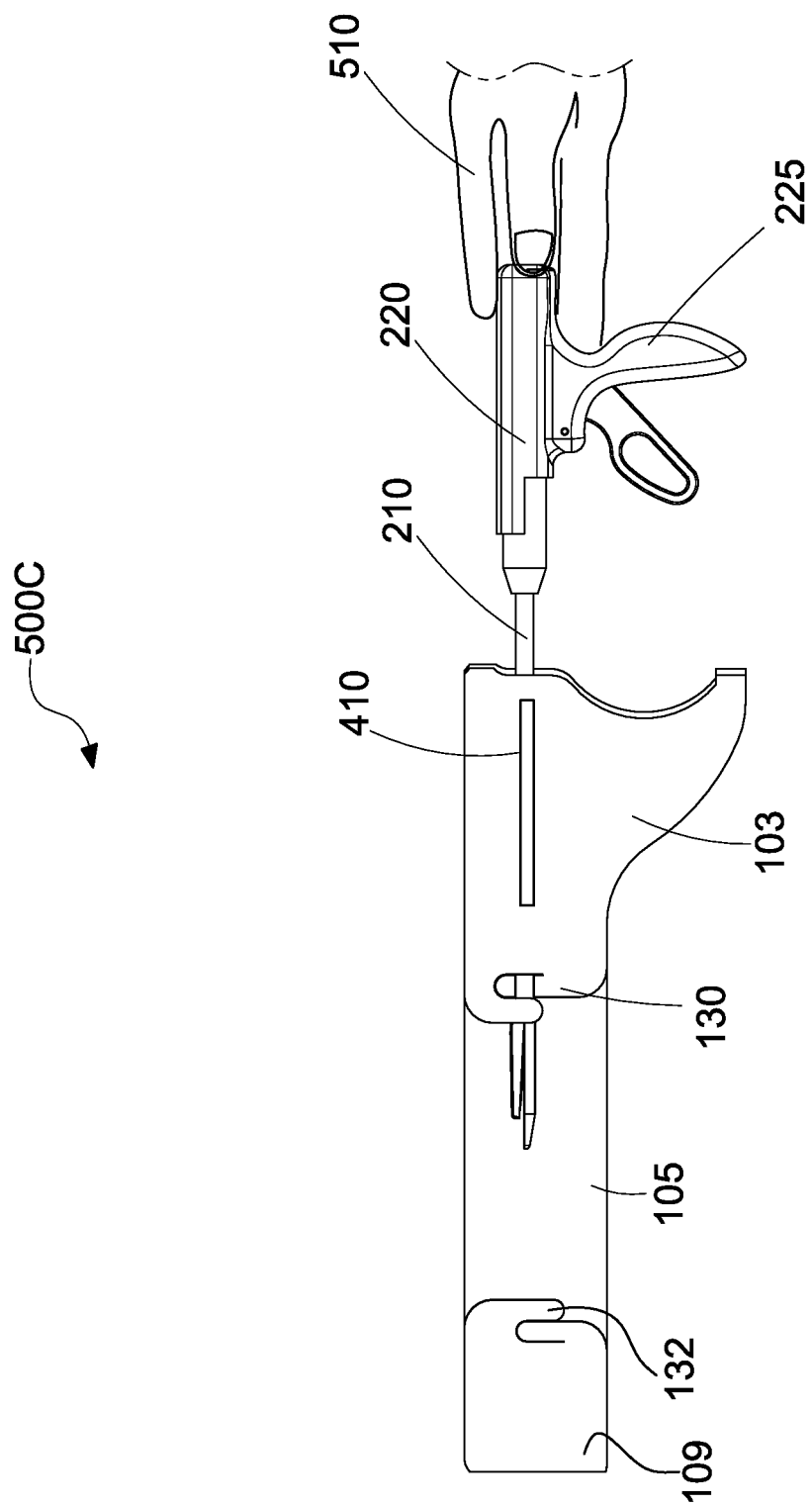
FIG. 5C illustrates a user pulling on the handle portion of the surgical instrument when the foldable sleeve is in the folded configuration, and completely removing the handle portion of the surgical instrument, in accordance with the embodiments of the present disclosure.

FIG. 5C illustrates a third configuration 500C where the user's hand 510 pulls on the body portion 220 or the handle portion 225 of the surgical instrument 200 when the foldable sleeve 100 is in the folded configuration, and completely removes the handle portion 225 of the surgical instrument 200 from the foldable sleeve 100 without having to unlock the tabs 130, 132, in accordance with the embodiments of the present disclosure.

FIGS. 6A-6C illustrate how the foldable sleeve 100 is transitioned from the unfolded configuration to the folded configuration, in accordance with the embodiments of the present disclosure.

FIG. 6A depicts a first configuration 600A of the unfolded sleeve 100, FIG. 6B depicts a second configuration 600B where the panels 103, 109 are folded onto panel 105, and FIG. 6C is a third configuration 600C that depicts the folded sleeve 100. FIGS. 6A-6C illustrate that the sleeve 100 of the exemplary embodiments of the present disclosure aids in the volume of waste being reduced in the operating room (OR). For example, after removing the surgical instrument 200 from the sleeve 100, the sleeve 100 may be folded back into a substantially flat configuration (see FIG. 6C), such that it occupies the least amount of space possible. Thus, the substantially flat configuration of the sleeve 100 creates less waste when disposed of, as opposed to traditional methods of packaging.

Therefore, in summary, a sleeve is made of one piece of, for example, paperboard that has two pre-cut sections or strips through which the shaft of a surgical instrument is inserted. The sleeve wraps the surgical instrument on both ends via a continuous set of spaced apart creases. The two ends of the sleeve include two sets of lock tabs that lock against the shaft of the instrument and secure the entire assembly. A wide opening is present on the sleeve toward the proximal end of the sleeve that allows the user to access the surgical instrument without having to remove the sleeve and instrument assembly or unlock the tabs of the sleeve. The sleeve may also have a window to display the product name and other relevant information.

Additionally, each foldable sleeve may be packaged within a foil pouch. The foil pouch may be part of a kit. In one exemplary embodiment, the kit may include a package containing at least one surgical instrument and at least one foldable sleeve configured to retain the at least one surgical instrument. The at least one surgical instrument may be one of a grasper, cutter, scissor, clip applier, stapler, dissector, retractor, access device, clamping device, vessel expanding device, biopsy device, drug/gene therapy delivery device, energy delivery device, and a drill, or any other surgical instrument used for performing a surgical procedure. The package may further include instructions for use.

The foldable sleeve is designed to provide an easy one-hand product access or dispensing feature. The wide opening on the sleeve toward the chevron end of the pouch allows the user to access the surgical instrument without having to remove the sleeve and instrument assembly from the pouch or unlock any tabs on the sleeve. This feature helps save an entire operational step for the nurses or surgeons in the operating room, thereby reducing an amount of time required to prepare surgical instruments for surgery. In addition, this sleeve, which may be a paperboard sleeve, still provides the ability to transfer the surgical instrument encased or enveloped within the sleeve to the sterile field.

Further advantages of the present disclosure include significant cost reductions due to the use of a paper-based product. Such cost reductions in turn can have a beneficial impact on the environment through, for example, reducing oil and other energy consumption associated with manufacturing and/or shipping and handling. With growing concerns for the environment, including global warming concerns for example, it is desirable to address the drawbacks of the amount of waste derived from current packaging for various consumer products, including medical instrument products. For example, it is desirable to provide "green," or environmentally friendly packaging alternatives that can reduce waste and/or are made substantially of renewable resources. It is also desirable to be able to reduce the overall size of the packaging as a way to reduce waste. The foldable sleeve of the present disclosure meets such requirements and accomplishes such goals. The foldable sleeve may be formed or manufactured from any type of material or combination of materials that are readily foldable and recyclable, such as paperboard, cardboard, or plastics.

Further advantages of the present disclosure include significant cost reductions due to the light-weight nature of the paper-based product. The novel foldable sleeve of the exemplary embodiments of the present disclosure provides for low cost manufacturing, excellent performance, improved quality, high strength and the replacement of heavy-weight packaging materials. Thus, the packaging allows for a significant reduction in material required to manufacture the foldable sleeve. Additionally, the light-weight nature and design (smaller external packaging) of the foldable sleeve of the exemplary embodiments of the present disclosure allows for reduced shelf space in the operating room. Also, blister packages use too much space when packaged in, for example, a box as they are designed in larger, bulkier configurations, and are not easily compactible when disposed of in the operating (OR). In contrast, the foldable sleeve of the exemplary embodiments of the present disclosure is compactible. When the sleeve is in a folded configuration to be packaged within a box, the sleeve occupies a small amount of space within the box, thus resulting in efficient packaging. Efficient packaging results in more sleeves being fitted within each box, thus reducing the number of boxes required for shipping and, thus, optimizing product delivery and minimizing the environmental footprint. Further, easier disposal within the OR is achieved by more efficiently folding the sleeve (once the surgical instrument is removed) to occupy the least amount of space.

Further advantages of the present disclosure include significant cost reductions due to the recyclable nature of paper and the foldable sleeve. It is environmentally and economically advantageous to manufacture packaging material from components that are more durable and thereby can be reused more often, made with recycled materials, recyclable themselves, can be safely incinerated or are naturally degradable. This helps the environment and eliminates the ever-increasing costs of special handling and/or waste disposal associated with non-recyclable material. The foldable sleeve of the present disclosure meets such requirements and facilitates recycling.

Moreover, another advantage of using the foldable sleeve of the exemplary embodiments of the present disclosure is that instructions or information or indicia may be printed directly onto the foldable sleeve without the need to use additional components, thus reducing the number of components used to package a product, such as a surgical instrument.

It is to be understood that the various embodiments shown and described herein are to be taken as exemplary. Elements and materials, and arrangements of those elements and materials, may be substituted for those illustrated and described herein, parts may be reversed, and certain features of the present disclosure may be utilized independently, all as would be apparent to one skilled in the art after having the benefit of the description herein. Changes may be made in the elements described herein without departing from the spirit and scope of the present disclosure and following claims, including their equivalents. It is to be understood that the particular examples and embodiments set forth herein are non-limiting, and modifications to structure, dimensions, materials, and methodologies may be made without departing from the scope of the present disclosure.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

The invention claimed is:

1. A sleeve for retaining a surgical instrument, the sleeve comprising:
   a first panel, a second panel, and a third panel arranged in a series configuration, the first panel and the third panel are hingedly connected to the second panel and are selectively movable between an unfolded orientation and a folded orientation with respect to the second panel;
   at least one locking tab disposed on an end of the first panel; and
   an opening defined between the first panel and the second panel that is configured to expose at least a portion of the surgical instrument;
   wherein the sleeve is configured to allow the surgical instrument to be removed through the opening of the sleeve while the first panel and the third panel are in the folded orientation and a gap is defined between the first panel and the third panel when the first panel and third panel are in the folded orientation, such that the first panel is free from contact with the third panel when the first panel and the third panel are in the folded orientation.

2. The sleeve according to claim 1, wherein the sleeve is configured to allow the surgical instrument to be removed from the opening of the sleeve while maintaining the series configuration of the first panel, the second panel and the third panel.

3. The sleeve according to claim 1, wherein the at least one locking tab is configured to engage a section of the surgical instrument to help retain the surgical instrument at least partially within the sleeve.

4. The sleeve according to claim 1, wherein the sleeve is configured to allow the surgical instrument to be removed from the opening of the sleeve without unlocking the at least one locking tab.

5. The sleeve according to claim 1, wherein the at least one locking tab includes a first locking tab and a second locking tab, the first locking tab is configured to engage a first section of a shaft of the surgical instrument, and the second locking tab is configured to engage a second section of the shaft of the surgical instrument to help retain the surgical instrument at least partially within the foldable sleeve.

* * * * *